(12) United States Patent
Yoo et al.

(10) Patent No.: US 11,266,755 B2
(45) Date of Patent: Mar. 8, 2022

(54) DEVELOPMENT AND APPLICATION OF TUMOR DIAGNOSTIC RADIOACTIVE PROBE TARGETING FOLIC ACID RECEPTOR

(71) Applicant: Kyungpook National University Industry-Academic Cooperation Foundation, Daegu (KR)

(72) Inventors: Jeong Soo Yoo, Daegu (KR); Woong Hee Lee, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 57 days.

(21) Appl. No.: 16/700,629

(22) Filed: Dec. 2, 2019

(65) Prior Publication Data
US 2020/0101179 A1    Apr. 2, 2020

Related U.S. Application Data

(63) Continuation of application No. PCT/KR2018/006365, filed on Jun. 4, 2018.

(30) Foreign Application Priority Data

Jun. 2, 2017    (KR) .................. 10-2017-0069290

(51) Int. Cl.
| | |
|---|---|
| *A61K 51/00* | (2006.01) |
| *A61M 36/14* | (2006.01) |
| *A61K 51/12* | (2006.01) |
| *A61B 5/00* | (2006.01) |
| *A61B 6/03* | (2006.01) |
| *A61K 49/00* | (2006.01) |

(52) U.S. Cl.
CPC ........ *A61K 51/1234* (2013.01); *A61B 5/0071* (2013.01); *A61B 6/037* (2013.01); *A61K 49/0002* (2013.01)

(58) Field of Classification Search
CPC ............ A61K 51/1234; A61K 49/0002; A61B 5/0071; A61B 6/037
USPC ...................................................... 424/1.21
See application file for complete search history.

(56) References Cited

FOREIGN PATENT DOCUMENTS

| KR | 2010-0075412 A | 7/2010 |
|---|---|---|
| KR | 2012-0016032 A | 2/2012 |
| KR | 10-1469156 B1 | 12/2014 |
| KR | 2015-0128103 A | 11/2015 |

OTHER PUBLICATIONS

Pradhan et al. J. Controll. Release 142 (2010) 108-121.*
Hattori et al. J. Controll. Release 97 (2004) 173-183.*
Isreal et al. Appl. Radiat. Isot. 66 (2008) 513-522.*
International Search Report corresponding to PCT/KR2018/0066365 dated Feb. 8, 2019. (English Translation).
Kim et al., "Vivid Tumor Imaging Utilizing Liposome-Carried Bimodal Radiotracer," ACS Medicinal Chemistry Letters, vol. 5, pp. 390-394 (2014).
Bogdanov et al., "A new macromolecule as a contrast agent for MR angiography: preparation, properties, and animal studies." Radiology, vol. 187, pp. 701-706 (1993).
Office Action (Rejection) corresponding to Korean Patent Application No. 10-2018-0063751 dated Nov. 5, 2019 (English Translation).
Written Opinion of the International Searching Authority corresponding to International Application No. PCT/KR2018/0066365 dated Feb. 8, 2019. (English Translation).
International Preliminary Report on Patentability Corresponding to International Application No. PCT/KR2018/006365 dated Dec. 3, 2019.
Hattori et al., "Enhanced in vitro DNA transfection efficiency by novel folate-linked nanoparticles in human prostate cancer and oral cancer," K. Controll. Release, vol. 97, pp. 173-183 (2004).
Isreal et al., "Improved synthesis of no-carrier-added p-[$^{124}$I]iodo-L-phenylalanine and p-[$^{131}$I]iodo-L-phenylalanine for nuclear medicine applications in malignant gliomas," Appl. Radiat. Isot., vol. 66, pp. 512-522 (2008).
Pradhan et al., "Targeted temperature sensitve magnetic liposomes for thermo-chemotherapy," J. Controll. Release, vol. 142, pp. 108-121 (2010).

(Continued)

*Primary Examiner* — Michael G. Hartley
*Assistant Examiner* — Sean R Donohue
(74) *Attorney, Agent, or Firm* — Jenkins, Wilson, Taylor & Hunt, P.A.

(57) ABSTRACT

The present invention pertains to a novel liposome-based contrast agent that is for suppressing absorption in the reticuloendothelial system and for tumor-specific delivery of a radiolabeled substance. More specifically, the present invention pertains to: a liposome contrast agent containing a lipid and a compound of chemical formula 1, which is a radiolabeled substance, the liposome contrast agent being characterized in that the lipid is composed of (a) cholesterol, (b) 1,2-dipalmitoyl-sn-glycero-3-phosphocholine (DPPC), and (c) 1,2-distearoyl-sn-glycero-3-phosphoethanolamine-N [methoxy(polyethylene glycol)-2000] (DSPE-PEG2000); and a cancer diagnostic composition containing the liposome contrast agent as an active ingredient. If a liposome system, containing a contrast substance of chemical formula 1 having a unique lipid composition provided by the present invention, is manufactured, the tumor-to-organ uptake ratio of the contrast substance in the reticuloendothelial system increases significantly, thus greatly increasing the tumor diagnostic efficiency of the compound of chemical formula 1.

9 Claims, 17 Drawing Sheets

(12 of 17 Drawing Sheet(s) Filed in Color)

(56) References Cited

OTHER PUBLICATIONS

Tilcock et al., "Polymer-derivatized technetium 99mTc-labeled liposomal blood pool agents for nuclear medicine applications." Biochimica et Biophysica Acta, vol. 1148, pp. 77-84 (1993).

* cited by examiner

FIG. 6
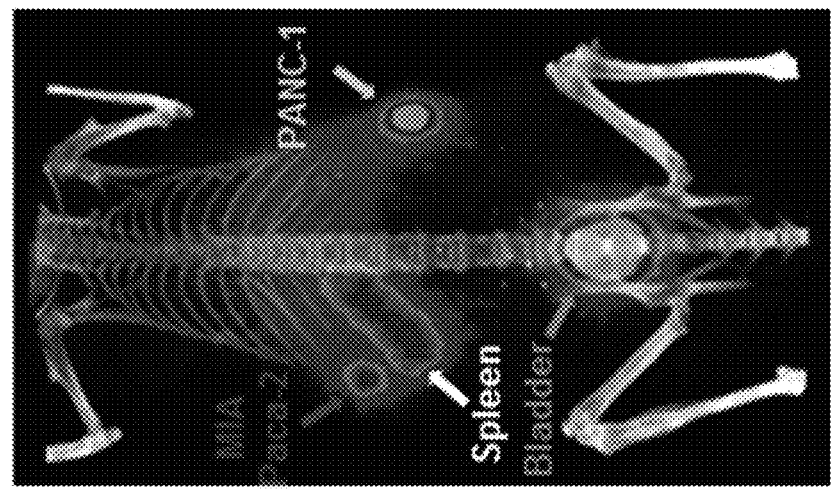
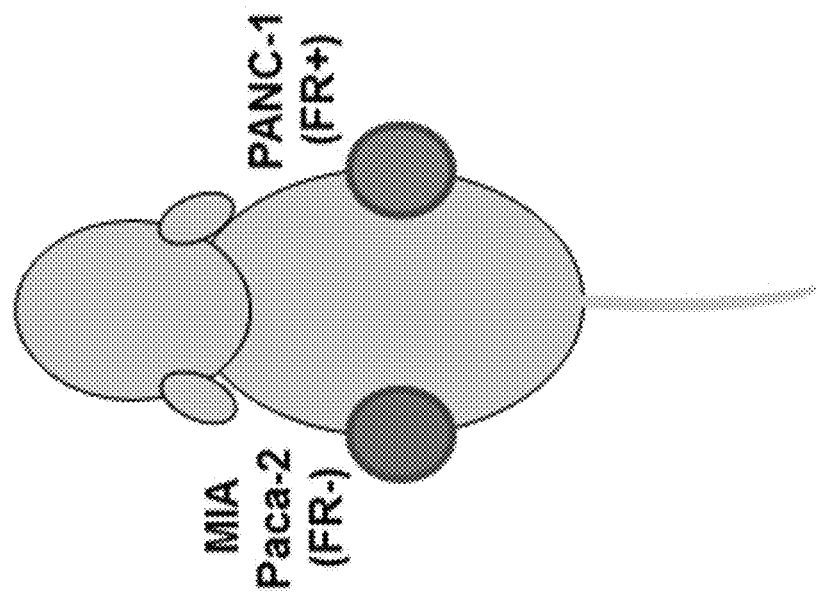

FIG. 11
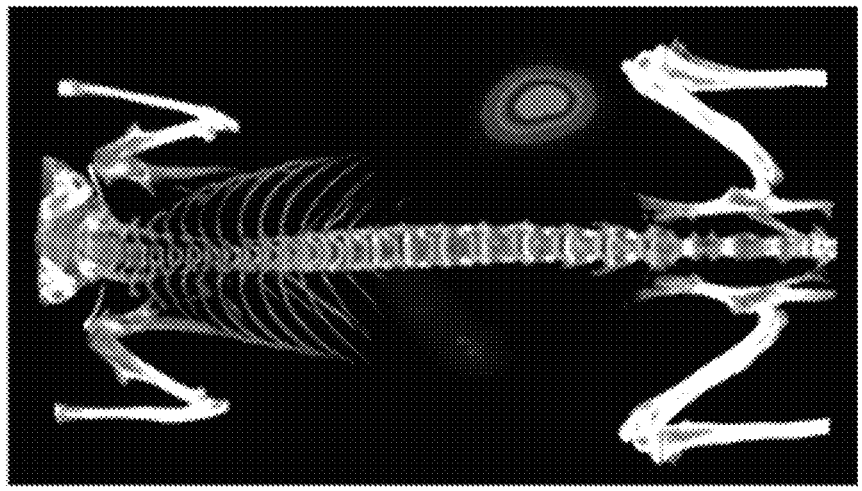
CT26
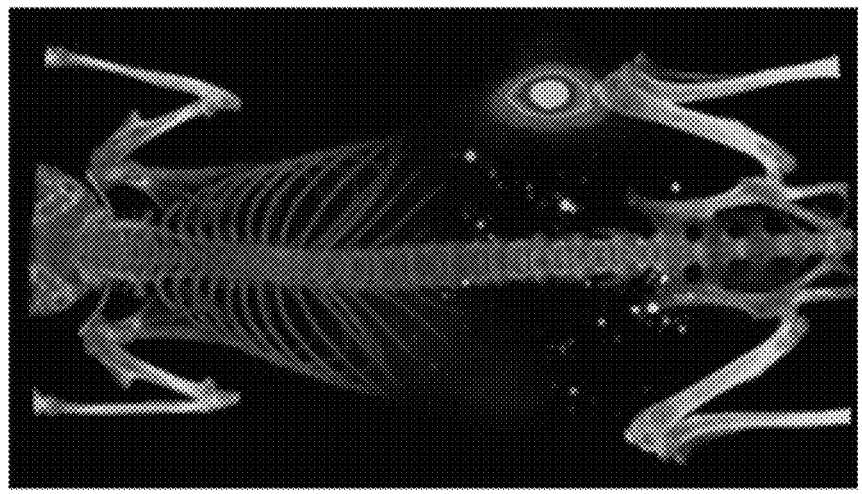
MDA-MB-231
4T1

DEVELOPMENT AND APPLICATION OF TUMOR DIAGNOSTIC RADIOACTIVE PROBE TARGETING FOLIC ACID RECEPTOR

CROSS REFERENCE TO RELATED APPLICATIONS

The present application is a continuation of PCT International Patent Application Serial No. PCT/KR2018/006365, filed Jun. 4, 2018, which claims priority from Korean Patent Application No. 10-2017-0069290, filed on Jun. 2, 2017, the entire contents of each of which are incorporated herein by reference.

TECHNICAL FIELD

The present invention relates to a novel liposome-based contrast agent for the inhibition of reticuloendothelial absorption and tumor-specific delivery of radioactive tracers, and more particularly to a liposome contrast agent characterized by consisting of a compound defined by Chemical Formula 1 as a radioactive tracer and lipid, wherein the lipid is characterized by consisting of (a) cholesterol; (b) 1,2-dipalmitoyl-sn-glycero-3-phosphocholine (DPPC); and (c) 1,2-distearoyl-sn-glycero-3-phosphoethanolamine-N[methoxy(polyethyleneglycol)-2000] (DSPE-PEG2000), and a cancer diagnostic composition containing the same as an active ingredient.

BACKGROUND OF THE INVENTION

Recently, liposomes have attracted much attention as carriers for delivering imaging probes to tissues in the body. Liposomes can be formulated to mount desired agents in an aqueous interior space (water soluble active ingredient) or in a lipid bilayer (water insoluble active ingredient).

However, liposomes have limitations in that control of drug release is inefficient and liposomes are quickly lost in the blood. In other words, the use of liposomes for site-specific delivery of active ingredients through the bloodstream is also limited by the rapid removal of liposomes from the blood by cells of the reticuloendothelial system (RES). In this regard, hydrophilic polymers, such as polyethylene glycol (PEG), has been found to reduce absorption by RES when placed on the surface of the material (C. Tilcock et al., Biochimica et Biophysica Acta. 1148, pp. 77-84 (1993); A. A. Bogdanoy et al., Radiology, 187, pp. 701-706 (1993)). In practice, however, simply incorporating PEG into liposomes is not sufficient, and the effects on inhibition of absorption by the RES system vary widely depending on the specific composition of the phospholipids, the composition ratio, and the like.

Meanwhile, the development of intelligent formulations that have little interactions in normal organs (tissues) and allow the components encapsulated in the liposomes to function only in the diseased tissues such as cancer are attracting attention. There are needs for carriers which are stable to dilution after administration into the body, and can avoid biological barriers (e.g., absorption of the reticuloendothelial system) as well as deliver desired components specifically in response to the physiological environment encountered in diseased tissues such as solid tumors.

Liposomes are normally not leaky, but may leak if, for example, the liposome membrane is punctured, decomposes or dissolves, or the membrane temperature is increased to the phase transition temperature. Hyperthermia at a target site in an individual can raise the liposome temperature above the phase transition temperature, thus causing the release of the liposome contents. Such sensitivity can be used for selective delivery of the desired agent. However, this technique may be of limited use if the phase transition temperature of liposomes is significantly higher than normal tissue temperature. This phase transition temperature can vary widely depending on the specific composition of the liposome (type, structure and composition ratio of lipids constituting the liposome). It is also known that the length of the hydrocarbon chain of the lipid can have a considerable influence on the membrane permeability of the phospholipid bilayer.

Imaging techniques of biological targets have to be excellent in terms of 1) sensitivity, 2) accuracy, and 3) rapidity because they are important tools for understanding biological phenomena or for accurate diagnosis of various diseases (patent document 1). However, the development of formulations that can substantially meet these requirements simultaneously involves a number of difficulties. In other words, for an accurate tumor diagnosis, it is important to simultaneously achieve specific absorption of the contrast agent at the tumor site and a significant reduction in background noise in other tissues and blood. All these are intricately linked with the characteristics of the target organ tissues, specificity of the contrast material, delivery methods of the contrast material, as well as the composition of the delivery formulation. Since it is very difficult to constitute the most suitable operating system for a specific contrast materials to be effective in the actual tissue and to adjust the ratio between the components, development of formulations and system to overcome such complexity involves hardships. Thus, there is still a need for a liposome system that can be used to efficiently deliver the target components.

DETAILED DESCRIPTION OF THE INVENTION

Technical Problem

Accordingly, the present inventors, while researching to prepare the most suitable intelligent formulation for the contrast agent defined by Chemical Formula 1 of the present invention, found out that a liposome system prepared and equipped with the contrast material of Chemical Formula 1 with a unique lipid composition provided by the present invention had significantly improved the tumor-to-organ uptake ratio and the accumulation rate of the contrast agent in tumors compared to RES organs as well as greatly shortening the image acquisition time, thereby completing the present invention.

Thus, an aspect of the present invention is to provide a liposome contrast agent consisting of a compound defined by Chemical Formula 1 and lipid, wherein the lipid is characterized by consisting of (a) cholesterol; (b) 1,2-dipalmitoyl-sn-glycero-3-phosphocholine (DPPC); and (c) 1,2-distearoyl-sn-glycero-3-phosphoethanolamine N[methoxy(polyethyleneglycol)-2000] (DSPE-PEG2000):

<Chemical Formula 1>

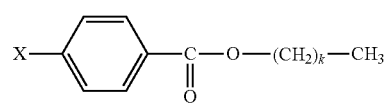

In the Chemical Formula 1, X is a radioisotope of iodine, and k is in a range of 5≤k≤30.

Another aspect of the present invention is to provide a liposome contrast agent consisting of a compound defined by Chemical Formula 1 and lipid, wherein the lipid is characterized by consisting essentially of (a) cholesterol; (b) 1,2-dipalmitoyl-sn-glycero-3-phosphocholine (DPPC); and (c)

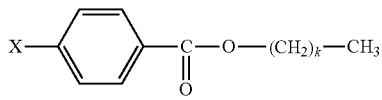

1,2-distearoyl-sn-glycero-3-phosphoethanolamine-N [methoxy (polyethyleneglycol)-2000] (DSPE-PEG2000):
<Chemical Formula 1>
In <Chemical Formula 1>, X is a radioisotope of iodine, and k is in the range of 5≤k≤30.

Another aspect of the present invention is to provide a cancer diagnostic composition comprising the above mentioned liposome contrast agent as an active ingredient.

Another aspect of the present invention is to provide a cancer diagnostic composition consisting of the above mentioned liposome contrast agent as an active ingredient.

Another aspect of the present invention is to provide a cancer diagnostic composition consisting essentially of the above mentioned liposome contrast agent as an active ingredient.

Another aspect of the present invention is to provide use of the above mentioned liposome contrast agent for the preparation of a diagnostic agent for cancer.

Another aspect of the present invention is to provide a method for diagnosing a cancer in a subject, the method comprising administering an effective amount of the above mentioned liposome contrast agent to the subject in need thereof.

Technical Solution

An embodiment according to an aspect of the present invention provides a liposome contrast agent consisting of a compound defined by Chemical Formula 1 and lipid, wherein the lipid is characterized by consisting of (a) cholesterol; (b) 1,2-dipalmitoyl-sn-glycero-3-phosphocholine (DPPC); and (c)

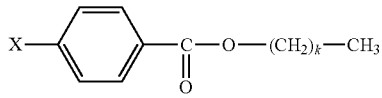

1,2-distearoyl-sn-glycero-3-phosphoethanolamine-N [methoxy(polyethyleneglycol)-2000] (DSPE-PEG2000):
<Chemical Formula 1>
In <Chemical Formula 1>, X is a radioisotope of iodine, and k is in the range of 5≤k≤30.

Another embodiment according to an aspect of the present invention provides a liposome contrast agent consisting of a compound defined by Chemical Formula 1 and lipid, wherein the lipid is characterized by consisting essentially of (a) cholesterol; (b) 1,2-dipalmitoyl-sn-glycero-3-phosphocholine (DPPC); and (c) 1,2-distearoyl-sn-glycero-3-phosphoethanolamine-N[methoxy (polyethyleneglycol)-2000 (DSPE-PEG2000):

<Chemical Formula 1>
In <Chemical Formula 1>, X is a radioisotope of iodine, and 5≤k≤30.

Another embodiment according to an aspect of the present invention provides a cancer diagnostic composition comprising the above mentioned liposome contrast agent as an active ingredient.

Another embodiment according to an aspect of the present invention provides a cancer diagnostic composition consisting of the above mentioned liposome contrast agent as an active ingredient.

Another embodiment according to an aspect of the present invention provides a cancer diagnostic composition consisting essentially of the above mentioned liposome contrast agent as an active ingredient.

Another embodiment according to an aspect of the present invention provides use of the above mentioned liposome contrast agent for the preparation of a diagnostic agent for cancer.

Another embodiment according to an aspect of the present invention provides a method for diagnosing a cancer in a subject, the method comprising administering an effective amount of the above mentioned liposome contrast agent to an

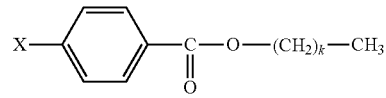

individual in need thereof.

Hereinafter, the present invention will be described in detail.

The present invention provides a liposome contrast agent

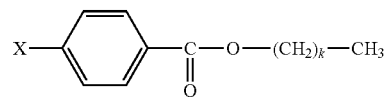

consisting of a compound defined by Chemical Formula 1 and lipid, wherein the lipid is characterized by consisting of
(a) cholesterol;
(b) 1,2-dipalmitoyl-sn-glycero-3-phosphocholine (DPPC); and
(c) 1,2-distearoyl-sn-glycero-3-phosphoethanolamine-N [methoxy (polyethyleneglycol)-2000] (DSPE-PEG2000):
<Chemical Formula 1>
In <Chemical Formula 1>, X is a radioisotope of iodine, and k is in the range of 5≤k≤30.

The liposome contrast agent of the present invention may be understood as a liposome-based in vivo delivery system loaded with a contrast material defined by the Chemical Formula 1.

In the present invention, the contrast material to be loaded on the liposome has a structure of the Chemical Formula 1, is not particularly limited in kind as long as it satisfies the condition that X is a radioisotope of iodine, and k is in the range of 5≤k≤30. X is not particularly limited in kind as long as it is known as a radioisotope of iodine (I). For example, X may be selected from the radioisotope group of iodine consisting of $^{122}I$, $^{123}I$, $^{124}I$, $^{125}I$, $^{131}I$ and $^{132}I$. The material having the structure of Chemical Formula 1 may be used in a dual manner for optical imaging or for positron emission tomography (PET) scanning.

Most preferably, the compound defined by Chemical Formula 1 may be hexadecyl-4-[$^{131}$I]iodobenzoate (referred to as [$^{131}$I] HIB) defined by <Chemical Formula 2>. In the present specification, hexadecyl-4-iodobenzoate corresponds to the compound of Chemical Formula 1 when k=15, and may be abbreviated as HIB.

<Chemical Formula 2>

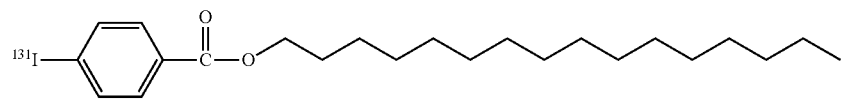

The present invention is distinguished from other liposome contrast systems in that the compound of Chemical Formula 1 (contrast agent) is loaded in the phospholipid bilayer of the liposome, and is not directly conjugated with the phospholipid (i.e., the contrast agent of the present invention is included in the liposome in a non-binding form with the phospholipid.)

In the liposome contrast agent of the present invention, the liposome serves as a carrier and it is the movement of the contrast material of Chemical Formula 1 loaded in the liposome which plays more important role for diagnosing a tumor. The liposome contrast agent of the present invention is characterized by functioning in a way that the liposome contrast agent itself or contrast material of Chemical Formula released from the liposomes accumulates inside the tumor tissues, whereas in the reticuloendothelial system, the contrast material of Chemical Formula 1 is released from the absorbed liposome contrast agent and excreted outside the body In order to allow this mode of action, it is required that the liposome will maintain adequate durability to endure the environment in the body (especially during blood transport) during the time the compound is transported and sensitivity such that the compound is released from the liposome or the liposome itself breaks down at the target site. Accordingly, unique lipid composition is needed which can impart such mode of action specifically for the compound of Chemical Formula 1 used in the present invention.

Therefore, the present invention discloses a special liposome composition which enables the compound of Chemical Formula 1 to have such mode of action in the body for the first time.

The liposome of the present invention is a unique system for tumor-specific delivery of the compound of the Chemical Formula 1, consisting of: (a) cholesterol; (b) DPPC; and (c) lipid of DSPE-PEG2000.

In the present invention, cholesterol may be a compound defined by Chemical Formula 3.

<Chemical Formula 3>

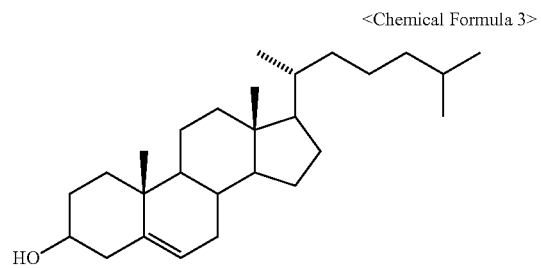 [SMILES: CC(C)CCC[C@@H](C)C1CCC2C3CC=C4CC(O)CC[C@]4(C)C3CC[C@@]21C]

In the present invention, DPPC may preferably be a compound defined by Chemical Formula 4.

<Chemical Formula 4>

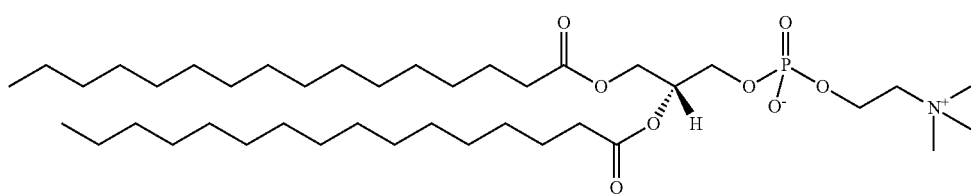

In the present invention, DSPE-PEG2000 may preferably be a compound defined by Chemical Formula 5.

<Chemical Formula 5>

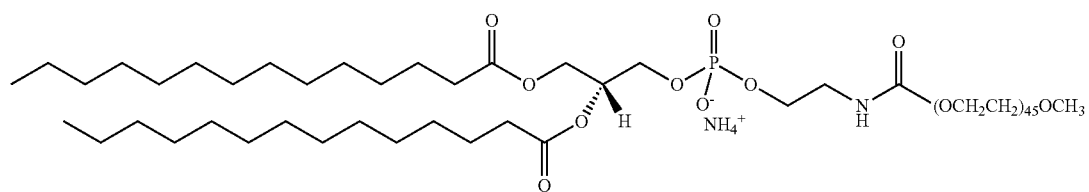

A molar ratio of lipid (a):(b):(c) is characterized by 1:(5 to 25):(3 to 15), preferably 1:(8 to 20):(4 to 13), more preferably, 1:(10 to 15):(6 to 10), and most preferably may of a molar ratio of 1:(11 to 13):(6 to 8).

The liposome contrast agent of the present invention having the lipid composition of (a), (b) and (c) is characterized by decreased absorption of the compound defined by Chemical Formula 1 in the reticuloendothelial system and increased absorption and accumulation of the compound defined by Chemical Formula 1 in tumors. In other words, the tumor-to-organ uptake ratio, comparing tumor versus RES organs, as well as the accumulation rate (retention rate) of the contrast agent were significantly enhanced. That is, when a liposome system equipped with the contrast agent of Chemical Formula 1 with a unique lipid composition provided by the present invention is prepared, it can efficiently deliver, release and accumulate the contrast agent in a tumor-specific manner, and at the same time, background noise in other tissues is greatly reduced. In addition, the liposome contrast agent of the present invention can significantly shorten the tumor image acquisition time when a PET is scanned using the compound of Chemical Formula 1.

In the mean time, among the lipid constituting the liposome contrast agent of the present invention, a part of the whole (c) DSPE-PEG2000 contained in a liposome may be attached to folate and.

The liposome contrast agent of the present invention may have a lipid composition consisting of (a) cholesterol;
(b) 1,2-dipalmitoyl-sn-glycero-3-phosphocholine (DPPC);
(c-1) 1,2-distearoyl-sn-glycero-3-phosphoethanolamine-N[methoxy(polyethyleneglycol)-2000] (DSPE-PEG2000); and
(c-2) 1,2-distearoyl-sn-glycero-3-phosphoethanolamine-N[methoxy(polyethyleneglycol)-2000-folate] (DSPE-PEG2000-folate).

In the present invention, DSPE-PEG2000-folate may preferably be a compound defined by Chemical Formula 6.

Preferably the tumor or cancer in the present invention may mean pancreatic cancer, breast cancer, colon cancer, ovarian cancer, cervical cancer, or melanoma. The lipid system of the present invention has a higher diagnostic value for the unique histological characteristics of pancreatic cancer, breast cancer, ovarian cancer, colon cancer, cervical cancer and melanoma among all other tumors.

The liposome contrast agent of the present invention is not particularly limited in its application as long as it is a means for imaging or visualizing the compound of Chemical Formula 1, for example, it can be used for optical imaging, positron emission tomography (PET) scanning, or single photon tomography scanning.

As described above, since the liposome contrast agent of the present invention has a specific diagnostic value for cancer (or tumor), the present invention also provides a cancer diagnostic composition comprising the liposome contrast agent of the present invention as an active ingredient.

In addition, the present invention provides use of the above mentioned liposome contrast agent for the preparation of a diagnostic agent for cancer.

In addition, the present invention provides a method for diagnosing a cancer in a subject, the method comprising administering an effective amount of the above mentioned liposome contrast agent to the subject in need thereof.

The term 'effective amount' of the present invention refers to an amount that exhibits an effect of diagnosing cancer when administered to an individual or an subject, and the term 'subject' includes an animal, preferably a mammal, particularly a human. It may be an animal, or may be a cell, tissue, organ or the like derived from the animal. The subject may be a patient in need of the said effect.

The term 'comprising' of the present invention is used in the same way as 'including' or 'characterized by' and does not exclude additional component elements or method steps not mentioned in terms of any particular composition or <Chemical Formula 6>

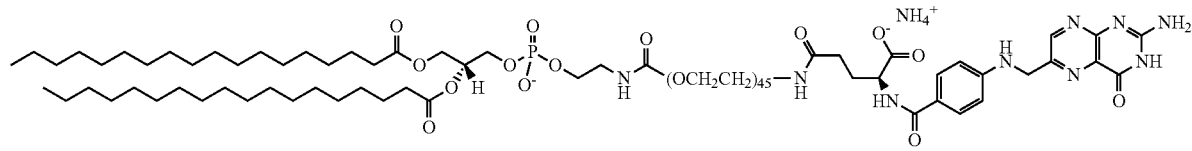

At this point, a molar ratio of the lipid (a):(b):(c-1):(c-2) may be characterized by 1:(5 to 25):(2 to 8):(1 to 7), preferably 1:(8 to 20):(3 to 8):(1 to 5), more preferably 1:(10 to 15):(4 to 6):(2 to 4), and most preferably, it may be of a molar ratio of 1:(11 to 13):(5 to 6):(1 to 2).

The liposome contrast agent of the present invention having the lipid composition of (a), (b), (c-1) and (c-2) is characterized by reduced absorption in the reticuloendothelial system as well as enhanced absorption of the compound defined by Chemical Formula 1 in the folate receptor overexpressing tumors.

The folate receptor overexpressing tumors may be selected from the group consisting of pancreatic cancer, breast cancer, ovarian cancer, lung cancer, cervical cancer, colon cancer, melanoma, kidney cancer, brain cancer, myeloid leukemia, and head and neck cancer, but is not limited thereto.

method. The term 'consisting of' means to exclude additional elements, steps or components, etc., unless otherwise noted. The term 'consisting essentially of' means within the scope of the composition or method, including the component elements or steps described, as well as the component elements or steps that do not substantially affect its basic properties, and the like.

Advantageous Effect

When a liposome system equipped with a contrast agent of Chemical Formula 1 with a unique lipid composition provided by the present invention is prepared, the tumor-to-organ uptake ratio as well as the accumulation rate of the contrast agent in tumors compared to RES organs is significantly increased, thereby highly enhancing diagnostic efficiency of the compound of Chemical Formula 1 for tumors.

BRIEF DESCRIPTION OF DRAWINGS/FIGURES

The patent or application file contains at least one drawing executed in color. Copies of this patent or patent application publication with color drawing(s) will be provided by the Office upon request and payment of the necessary fee.

FIG. 6 shows the PET imaging results 24 hours after administration of the liposome contrast agent according to the present invention to the tail vein after establishing a mouse xenograft model by injecting two different types of pancreatic cancer cells (PANC-1, MIA PaCa-2) with varying levels of folate receptor expression into both flanks of a single mouse, respectively.

FIG. 11 shows PET imaging results 24 hours after administration of the liposome contrast agent according to the present invention to the tail vein of the xenograft models using CT26 colorectal cancer cells or 4T1 and MDA-MB-231 breast cancer cells.

Figure 13A:
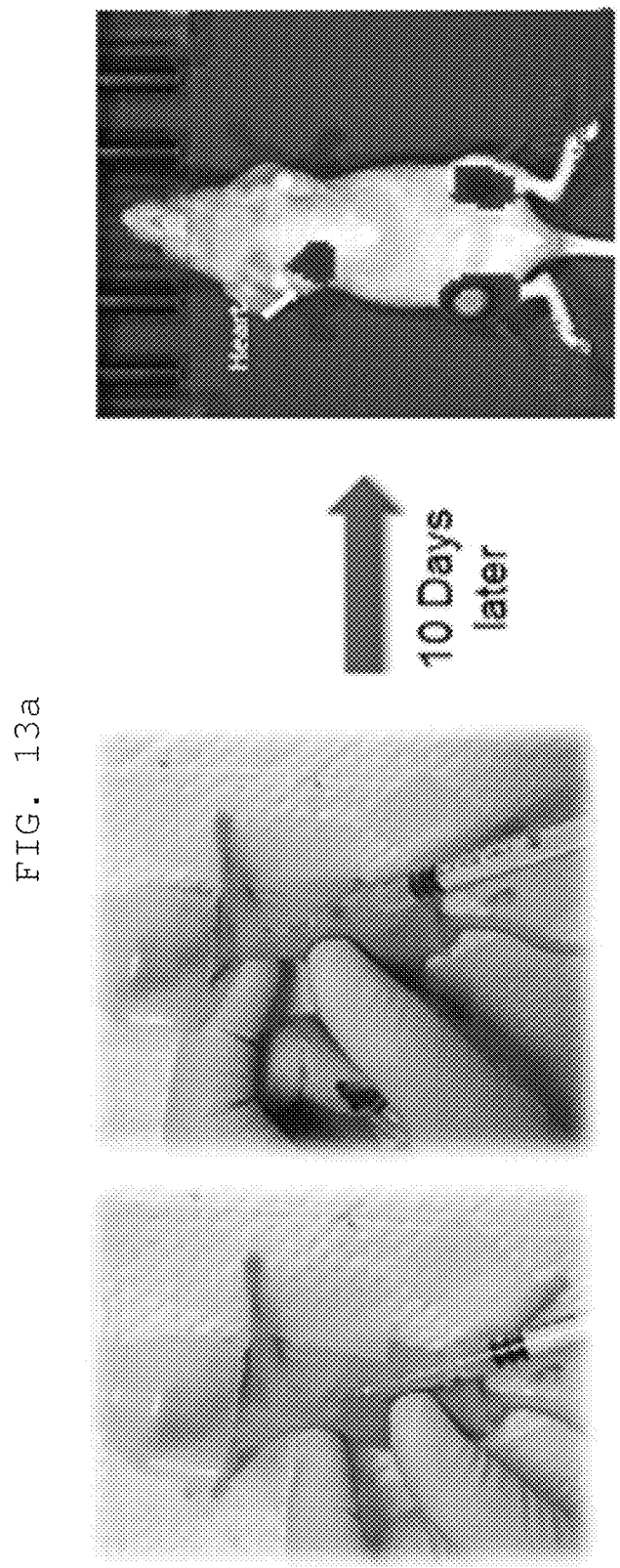
Figure 13B:
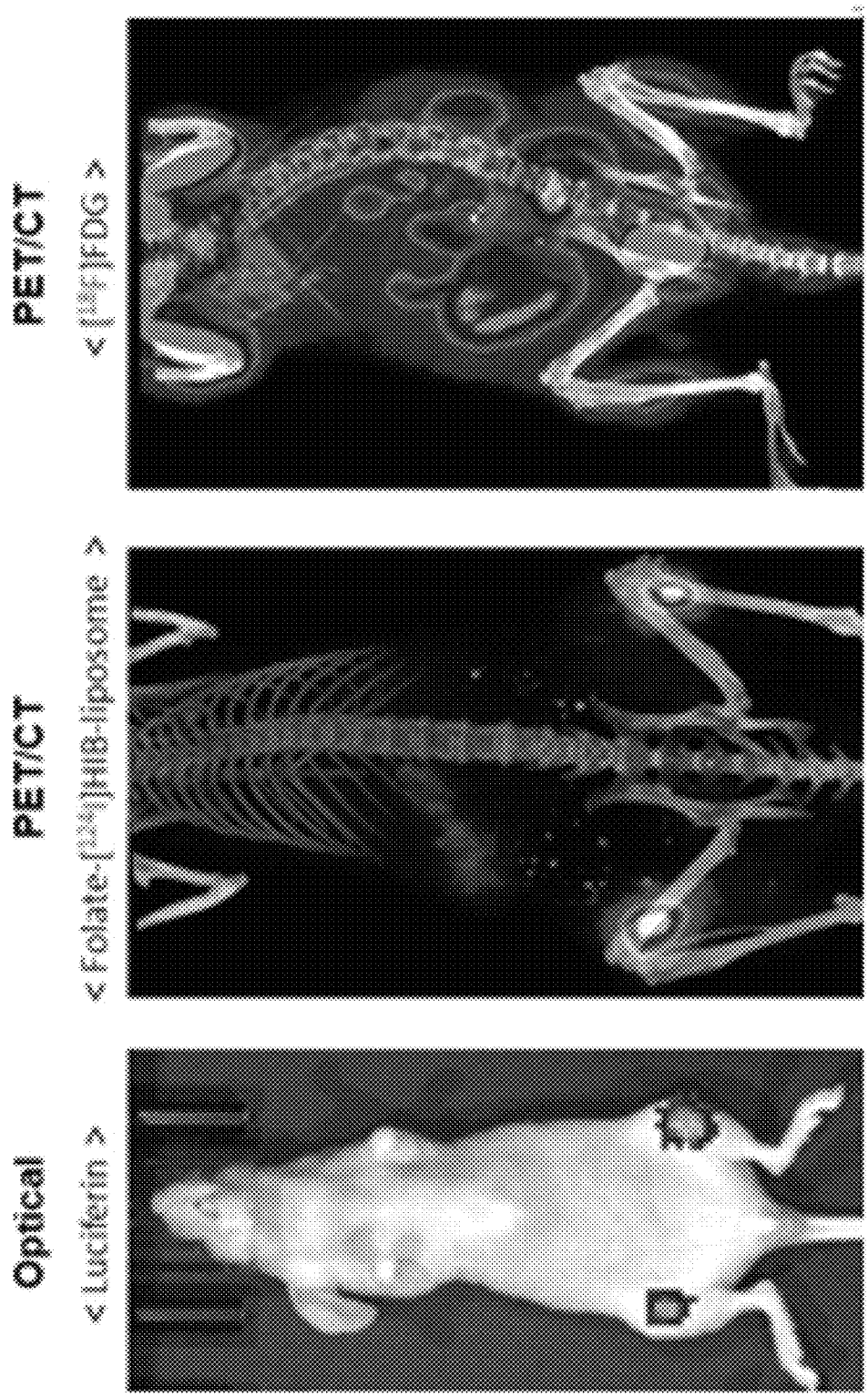
Figure 13C:
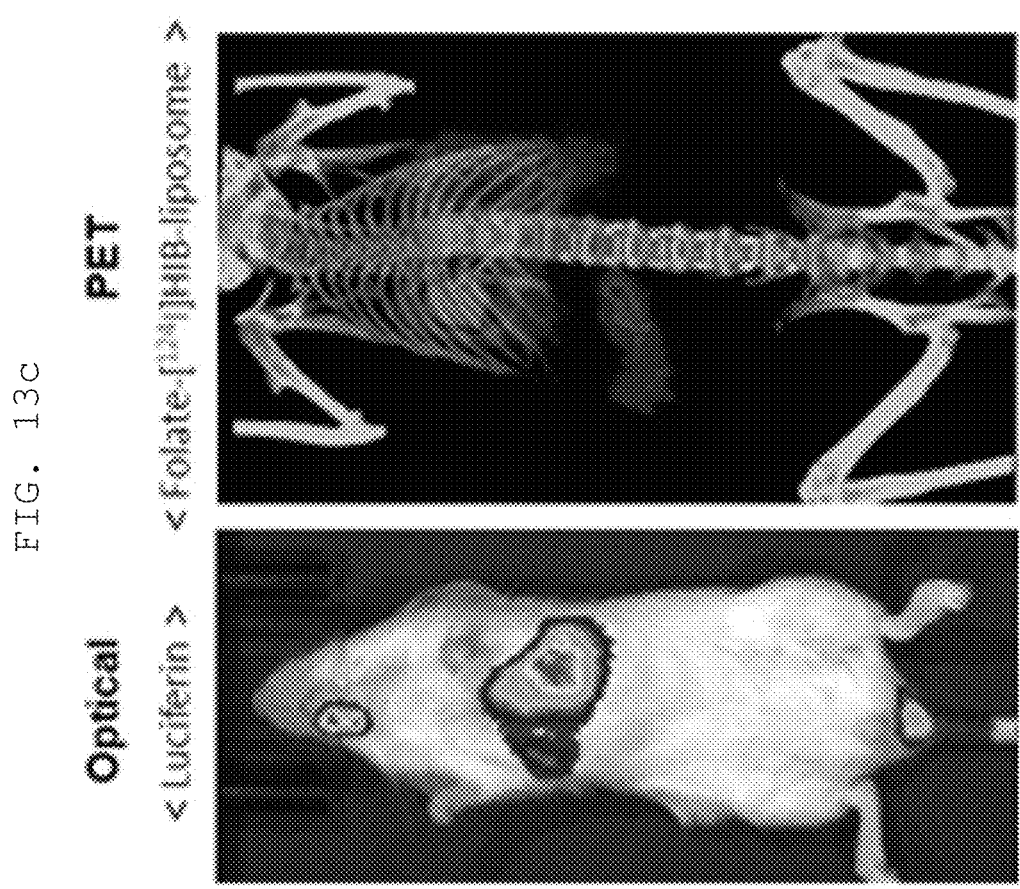

FIG. 13A, FIG. 13B or FIG. 13C each confirms the establishment of a breast cancer bone metastasis mouse model (FIG. 13A), and shows the PET imaging results 24 hours after administration of the contrast agent of the present invention after verifying the location of the metastasized tumor in the leg bone using luciferin luminescence imaging and the PET imaging results 1 hour after administration of [$^{18}$F] FDG to the tail vein in the same mouse model (FIG. 13B), or shows the PET or IVIS imaging results 24 hours after administration of the liposome contrast agent according to the present invention to the tail veins of the breast cancer lung metastasis model (FIG. 13C).

MODE FOR CARRYING OUT INVENTION

Hereinafter, the present invention will be described in more detail with reference to examples, experimental examples and manufacturing examples. However, the following examples, experimental examples and preparation examples are illustrative of the present invention, and the present invention is not limited to the following examples, experimental examples and manufacturing examples.

Example 1: Preparation of Liposomes Specialized for HIB

Figure 1:
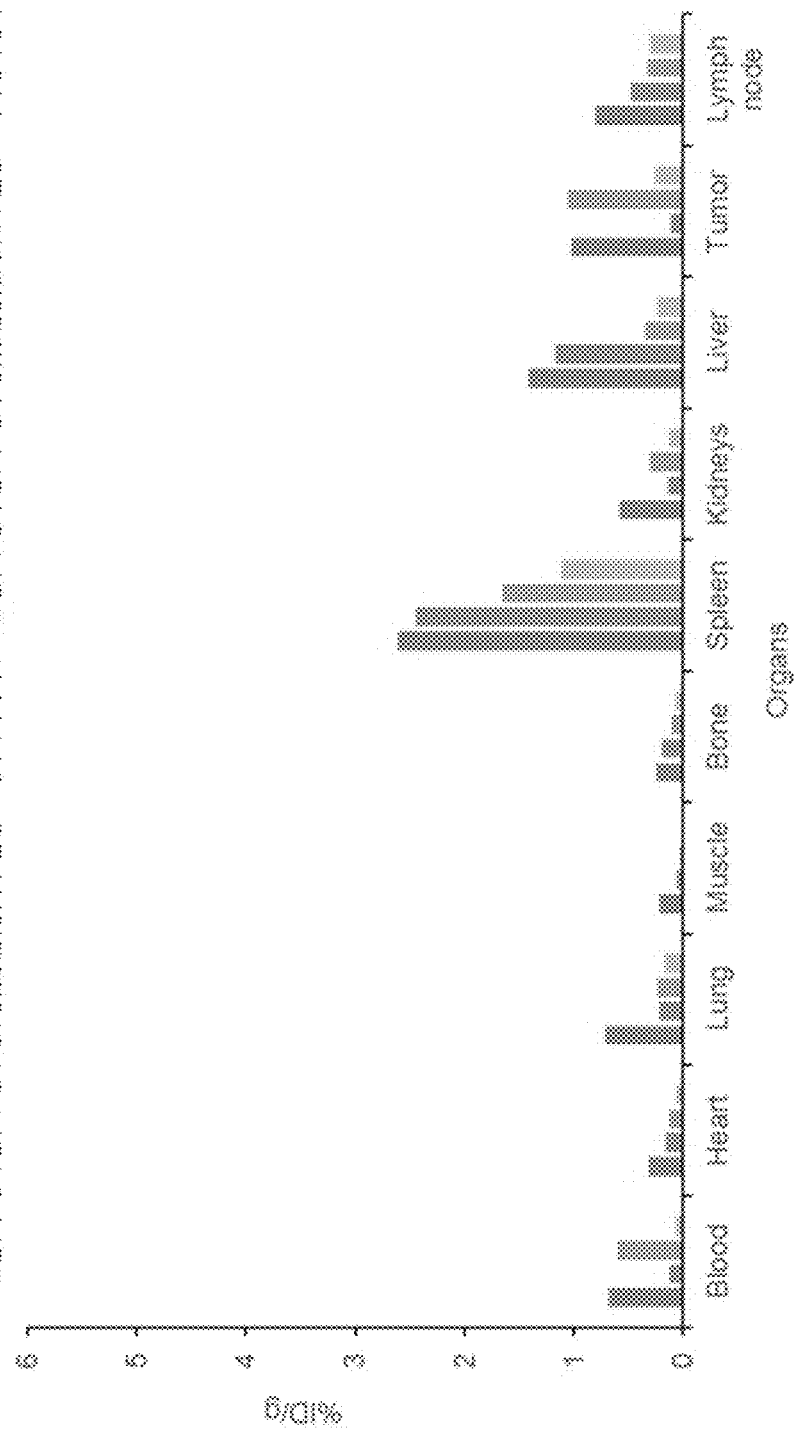
FIG. 1 shows the results of comparing degrees of HIB accumulation in tumors and other organs when liposomes were prepared with different composition ratios using DPPC, DPPG, cholesterol, and DSPE-PEG2000 (abbreviated as PEG).
Figure 2:
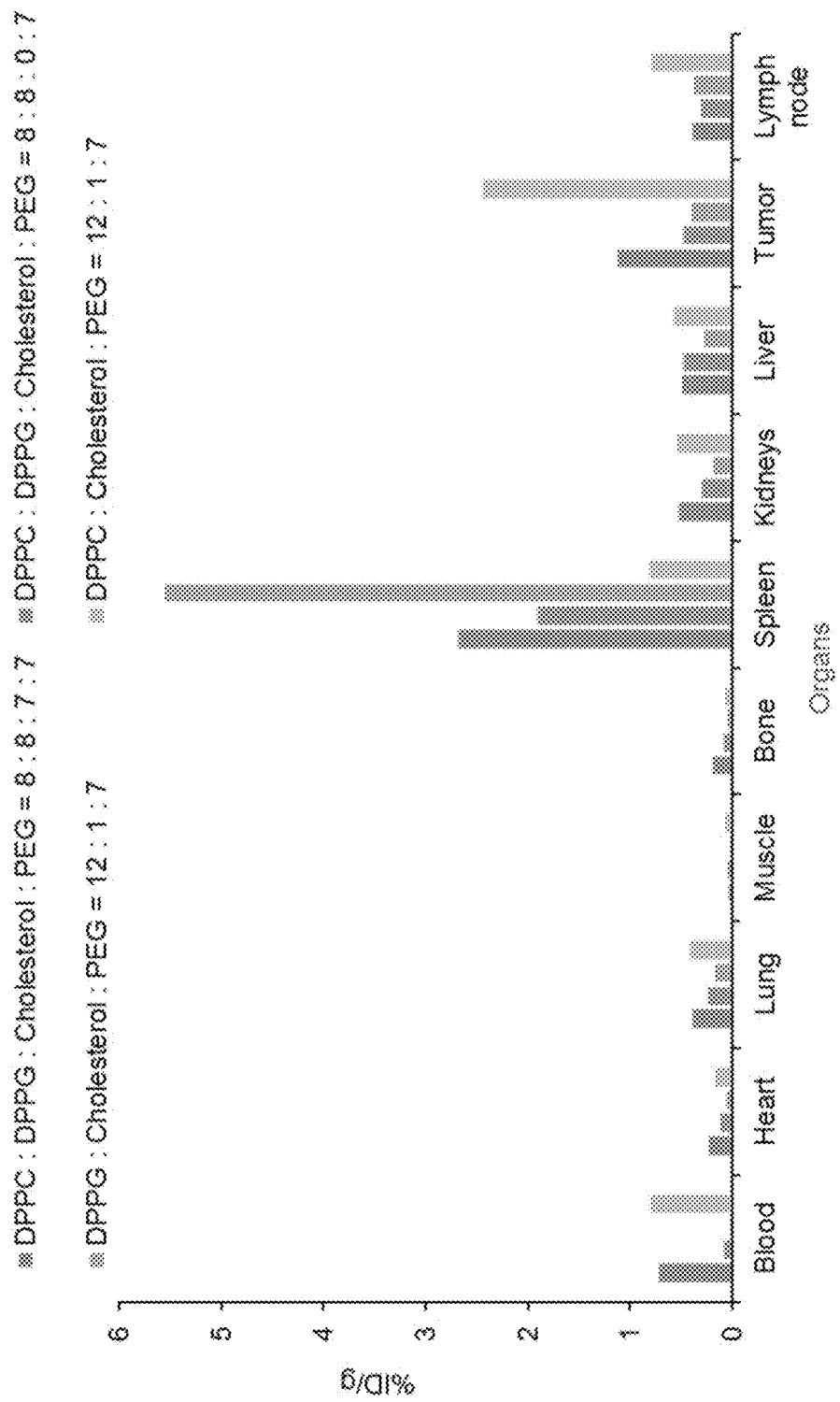
FIG. 2 shows the results examining the effect of DPPC or cholesterol on the delivery and the differential accumulation of HIB in tumors and other organs, respectively.

DPPC (1,2-dipalmitoyl-sn-glycero-3-phosphocholine), DPPG (1,2-dihexadecanoyl-sn-glycero-3-phospho-3-(1'-rac-glycero)), cholesterol, DSPE-PEG2000 (1,2-distearoyl-sn-glycero-3-phosphoethanolamine-N[methoxy (polyethyleneglycol)-2000]; abbreviated as PEG in figures and tables) were mixed according to the molar ratios as shown in FIG. 1 and FIG. 2, respectively (see Table 1 below). After mixing [$^{131}$I] HIB, thus prepared mixture was dried to obtain a thin lipid film. The lipid membrane was hydrated in saline for 25 minutes. Opaque liposome solution obtained as a result of hydration was extruded using a 100 nm membrane filter and further purified using a size exclusion column (PD-10, GE Healthcare), which generated liposome contrast agents loaded with [$^{131}$I] HIB having various lipid compositions.

TABLE 1

| No. | Lipid composition |
|---|---|
| 1 | DPPC:DPPG:cholesterol:PEG = 8:1:3:1 |
| 2 | DPPC:DPPG:cholesterol:PEG = 1:8:3:1 |
| 3 | DPPC:DPPG:cholesterol:PEG = 8:1:3:7 |
| 4 | DPPC:DPPG:cholesterol:PEG = 1:8:3:7 |
| 5 | DPPC:DPPG:cholesterol:PEG = 8:8:7:7 |
| 6 | DPPC:DPPG:cholesterol:PEG = 8:8:0:7 |
| 7 | DPPG:cholesterol:PEG = 12:1:7 |
| 8 | DPPC:cholesterol:PEG = 12:1:7 |

Afterwards, in order to examine in vivo distribution of liposomes of each composition in the mouse tumor model, experiments to verify biodistribution were performed by injection the liposome contrast agents (20 µCi) into the tail veins of CT26 cancer-BALB/C mice.

As a results as shown in FIG. 1, it was observed that the uptake of [$^{131}$I] HIB-labeled liposomes in the blood was maintained high while tumor uptake was at the level of 1% ID/g in the case of the liposome composition with reduced DPPG ratio. In addition, the liposome composition with reduced DPPC ratio showed a generally low uptake in the organ after injection and rapidly discharged into the body, while tumor uptake was significantly low.

And, as shown in FIG. 2, in the case of the compositions containing no cholesterol, the overall uptake of [$^{131}$I] HIB-labeled liposomes in the organs is reduced a lot, and the uptake in the tumors was not high either. On the contrary, in the case of the composition containing high cholesterol, the overall uptake in the organs increased and the intake in the tumors slightly increased. In addition, from the results from liposomes containing certain levels of cholesterol and PEG and only single type of lipid, (DPPG/DPPC:cholesterol: DSPE-PEG2000=12:1:7), it was observed that the difference in the uptake of tumors varied abruptly depending on the types of lipid. These findings suggest that the resulting effect cannot be predicted based on the specific types of lipid and composition ratios constituting liposomes even in the presence of PEG despite the previous report that inclusion of PEG generally reduced the liposome uptake in reticuloendothelial organs such as liver and spleen.

In the composition of liposomes using only DPPG as lipid, spleen uptake was particularly increased, and tumor uptake was markedly low. These results confirmed that the composition of liposomes greatly influenced the uptake by tumors and reticuloendothelial system, and the release and discharge of HIB loaded on the liposomes. It was also noted that a specific liposome composition ratio is required resulting in the optimal outcome in the tumor diagnosis using HIB.

Example 2: Verification of the HIB Specialization and the Effect of Folate Attachment Ratio 1-(hexadecyloxy)-4-iodobenzene (HIB-ether) was synthesized and radiolabeled with $^{131}$I to prepare [$^{131}$I] HIB-ether defined by the following Chemical Formula 7. After synthesizing liposomes with the lipid composition (see Table 2) shown in FIG. 3 using the same method as in Example 1, the liposome contrast agent according to Table 2 (20 μCi) was injected into the tail vein of the mouse grafted with pancreatic cancer cells (PANC-1) and biodistribution comparison experiments were performed 24 hours later.

was very large, and liver and spleen uptake of folate-[$^{131}$I] HIB-ether-liposome was much higher than folate-[$^{131}$I]HIB-liposome, which also increased the background noise level. In addition, liposomes of the composition excluding DSPE-PEG2000 (folate-[$^{131}$I]HIB-liposome (no PEG)) showed similar uptake pattern to folate-[$^{131}$I]HIB-liposome in most organs, while the degree of uptake in the liver was 6 times higher, and in contrast, it reduced down to approximately half level in the pancreatic cancer. On the basis of these results, use of HIB as a radioactive tracer is better for obtaining clear tumor images than that of HIB-ether for the diagnosis of pancreatic cancer, considering the uptake ratio of each organs and tumors (ratios of tumor to liver or spleen). In addition, the composition ratio constituting the liposomes was also found to be a very important factor in the effective diagnosis of the tumor.

Figure 4A:
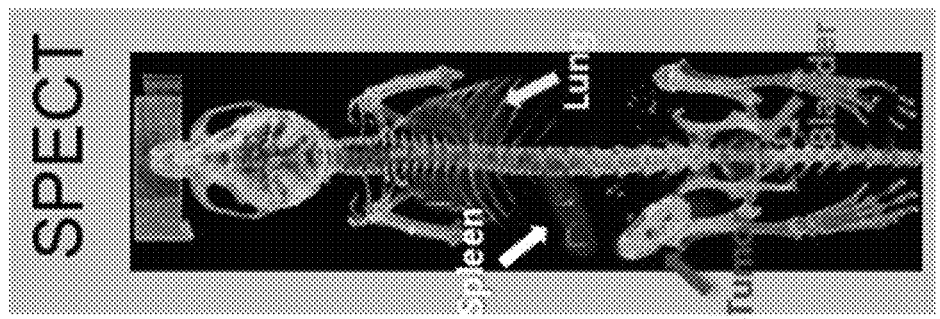
FIG. 4A and FIG. 4B show the results of SPECT imaging using the liposome contrast agent of the present invention in pancreatic cancer-induced mice (FIG. 4A) and normal mice (FIG. 4B).
Figure 4B:
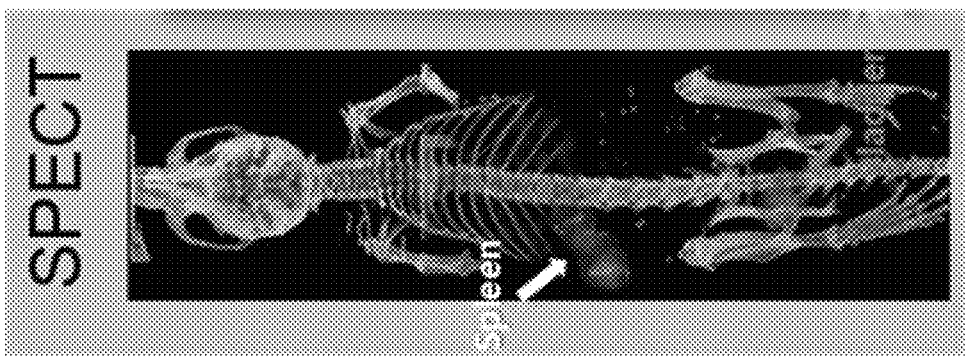

FIG. 4 shows the SPECT imaging results from the application of the liposome contrast agent of the present invention in pancreatic cancer-induced mice (A) and normal mice (B). In the pancreatic cancer model, it can be seen that the tumor is very clearly imaged compared to other neighboring organs.

Example 3: Evaluation of Cellular Uptake of the Liposome Contrast Agent In Vitro To evaluate the degrees of absorption of folate-[$^{124}$I]HIB-liposome prepared in Example 2 in tumor cells, tumor cells and normal cells derived from various tissues were examined for in vitro cellular uptake capacity.

After dispensing tumor cells or normal cells derived from each tissue 1×10$^5$ cells per well and allowing to adhere onto the surface of the culture dish, the folate receptor-targeting liposome contrast agents prepared in Example 2 (folate-[$^{124}$I] HIB-liposome) were applied, and the experiment was <Chemical Formula 7>

$^{131}$I—⟨benzene ring⟩—O—(long alkyl chain)

TABLE 2

| Type | Lipid composition |
| --- | --- |
| Folate-[$^{131}$I]HIB-liposome | DPPC:Cholesterol:DSPE-PEG2000:DSPE-PEG2000-folate = 12:1:5:2 |
| Folate-[$^{131}$I]HIB-ether-liposome | DPPC:Cholesterol:DSPE-PEG2000:DSPE-PEG2000-folate = 12:1:5:2 |
| Folate-[$^{131}$I]HIB-liposome(No PEG) | DPPC:Cholesterol:DSPE-PEG2000-folate = 12:1:2 |

In Table 2, "Folate-[$^{131}$I]HIB-liposome" means that [$^{131}$I] HIB is loaded in the liposomes having the lipid composition shown in the above table. The "Folate-[$^{131}$I]HIB-ether-liposome" indicates that [$^{131}$I]HIB-ether is loaded on the liposomes having the lipid composition shown in the above table. The "Folate-[$^{131}$I]HIB-liposome (No PEG)" refers to the liposomes loaded with [$^{131}$I]HIB having the lipid composition shown in the above table.

Figure 3:
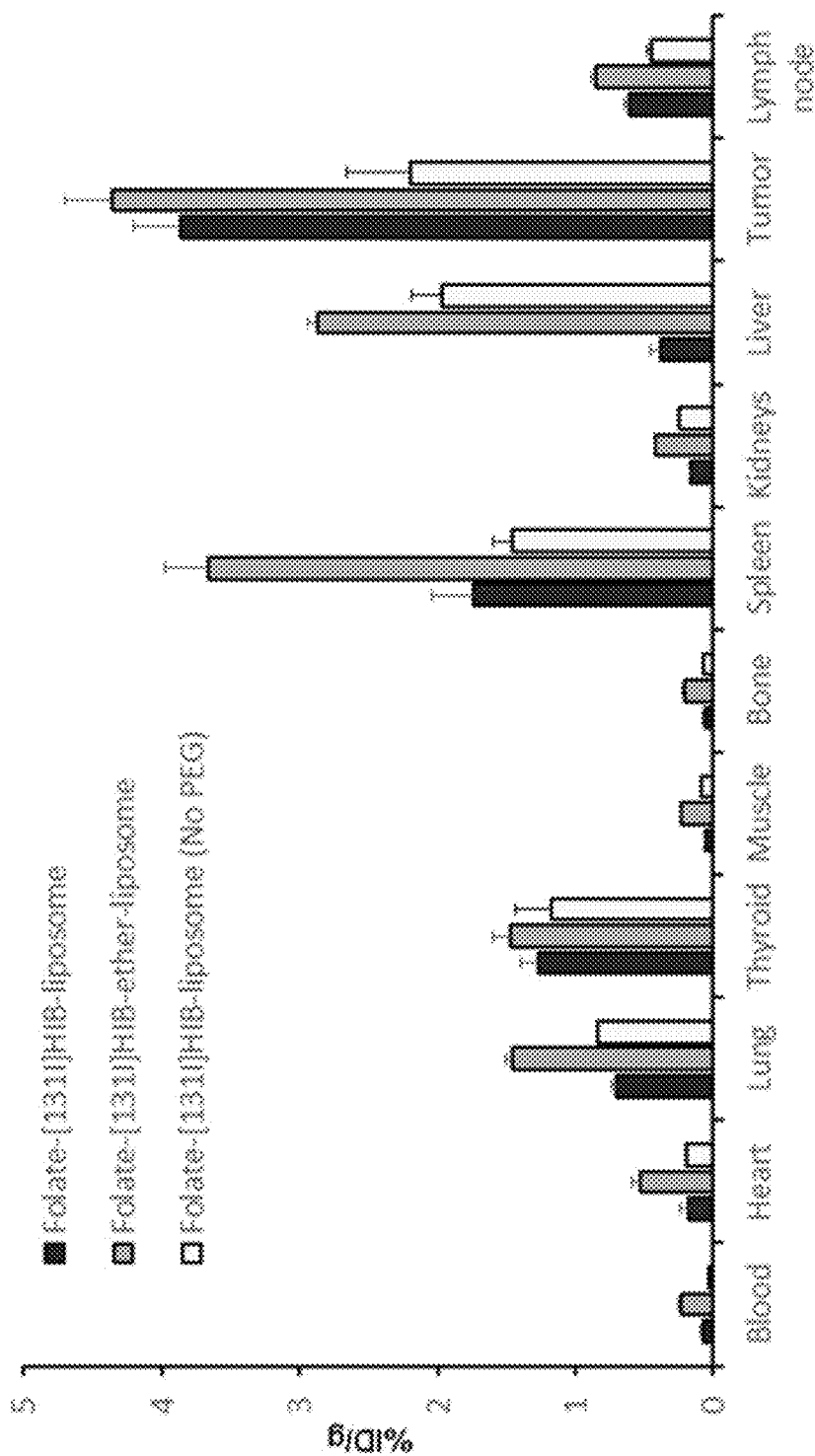
FIG. 3 shows the effect on the delivery and the differential accumulation of HIB in tumors and other organs according to the folate attachment rate and shows the results confirming that the liposome composition of the present invention is specific for HIB only in contrast to HIB-ether.

As shown in FIG. 3, the uptake of folate-[$^{131}$I]HIB-ether-liposome was higher than that of folate-[$^{131}$I]HIB-liposome in most organs, and the degrees of [$^{131}$I] HIB uptake for pancreatic cancer were similar. In particular, it was observed that the difference between the uptake of liver and spleen conducted to compare the degrees of cellular intake 12 hours and 24 hours after the treatment.

Normal cells: BNL CL.2 (liver), HEK293 (kidney), Raw264.7 (macrophage)

Tumor cells: MDA-MB-231 (breast cancer), B16F10 (melanoma), HeLa (cervical cancer), SKOV3 (ovarian cancer), CT26 (colorectal cancer), 4T1 (breast cancer)

Specifically, the cells were divided into 6 well plates 24 hours before the experiment and allowed to sufficiently adhere to the surface of the culture plate, then treated with folate receptor-targeting liposome contrast agent (folate-[$^{124}$I]HIB-liposome), 2 μCi per well. Subsequently cells were placed in the incubator for 12 hours or 24 hours and cultured for the time to ingest the liposomes.

After 12 hours and 24 hours, cells corresponding to each condition were first washed three times with PBS to remove all liposomes which did not get ingested into the cells, and then treated with trypsin-EDTA solution to release the cells from the bottom of the plate, transferred to a tube prepared in advance, and tubes corresponding to each condition was measured for radioactivity using gamma counter to check the cellular uptake.

Figure 5:
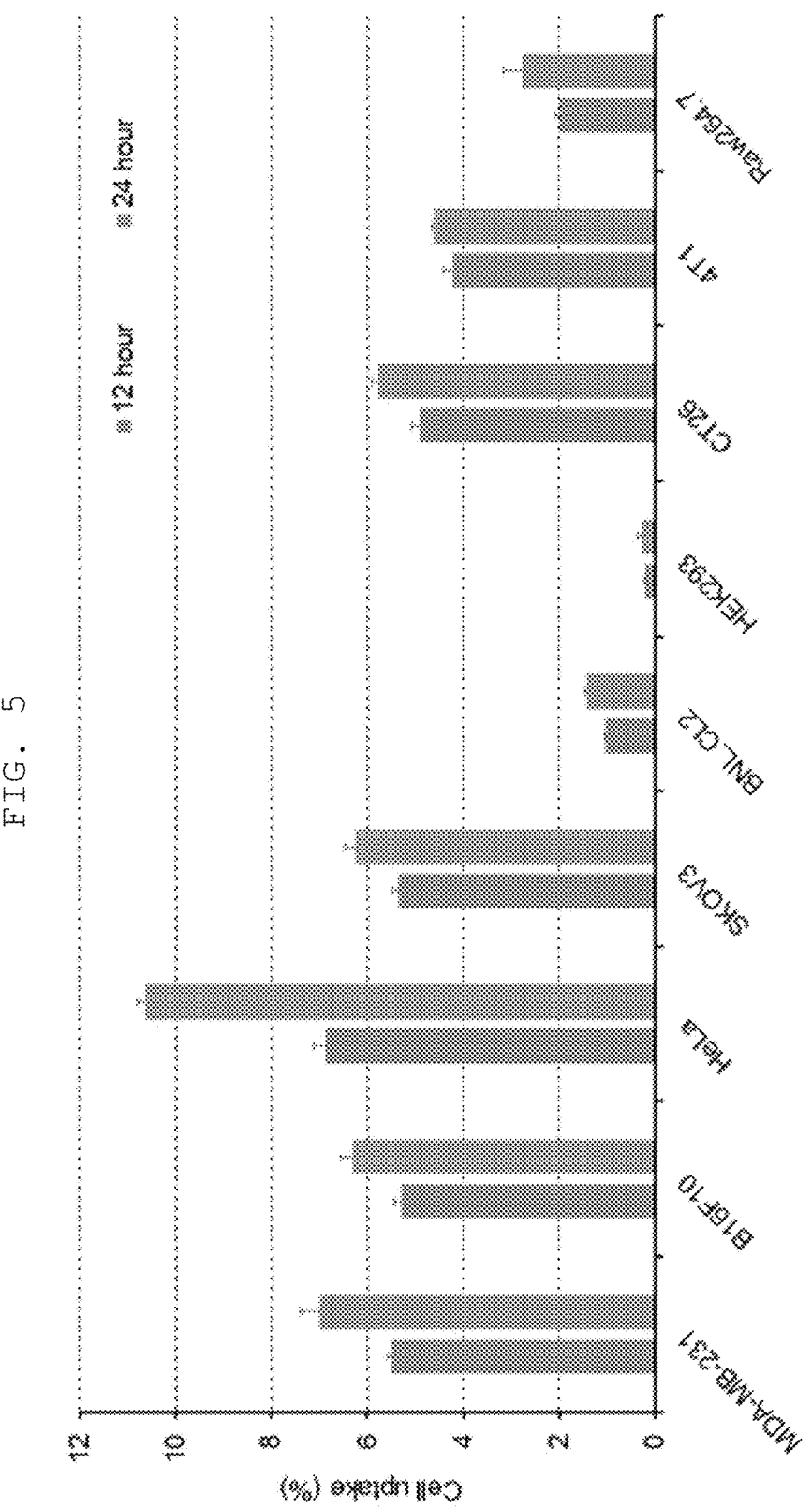
FIG. 5 shows the results evaluating degrees of absorption of liposomes according to the present invention in tumor cells or normal cells derived from various tissues.

The results are shown in FIG. 5.

Folate receptors are known to be expressed at higher levels in tumor cells than normal cells. As can be seen in FIG. 5, it was confirmed that the liposome contrast agent according to the present invention is uptaken greater in tumor cells overexpressing folate receptors compared with normal cells, proving that it can be useful as a radioactive probe for diagnosing various tumors.

Example 4: Confirmation of Specificity for Folate Receptor In Vivo

Two types of pancreatic cancer cells (PANC-1, MIA PaCa-2) were used for the pancreatic cancer xenograft models for the experiments. PANC-1 was characterized by overexpressing folate receptors, while MIA PaCa-2 is a pancreatic cancer cell line reported to have lower expression of folate receptors.

After injecting two types of pancreatic cancer cells into each flank of the same mouse to establish a xenograft model, the liposome contrast agent folate-[$^{124}$I]HIB-liposome) was injected into the tail vein (200 µCi) and PET scanning was carried out 24 hours later.

The results for this are shown in FIG. 6.

As shown in FIG. 6, signals were detected in both types of pancreatic cancer cells, but it was confirmed that a stronger signal was detected in the area grafted with PANC-1 cells overexpressing folate receptors. Namely, it can be said that the liposome contrast agent according to the present invention can diagnose tumors by actively targeting folate receptors.

Example 5: Evaluation of Liposome Absorption In Vivo

After confirming that the liposome contrast agent according to the present invention exhibits a very high absorption rate specifically for tumor cells in Example 3, the degrees of absorption of the liposome contrast agent in various tissues transplanted with tumor cells in the mouse model were measured.

Example 5-1: Xenograft Mouse Model

Cervical cancer cells (HeLa cells), ovarian cancer cells (SKOV3 cells), skin cancer (melanoma) cells (B16F10 cells) or colon cancer cells (CT26 cells) were injected in the right flank of mice. When tumors grew to a size of less than 1 cm, each organ was extracted 24 hours after the injection and the degree of absorption of the liposomes was evaluated.

The results are shown in FIG. 7 to FIG. 10.

Figure 7:
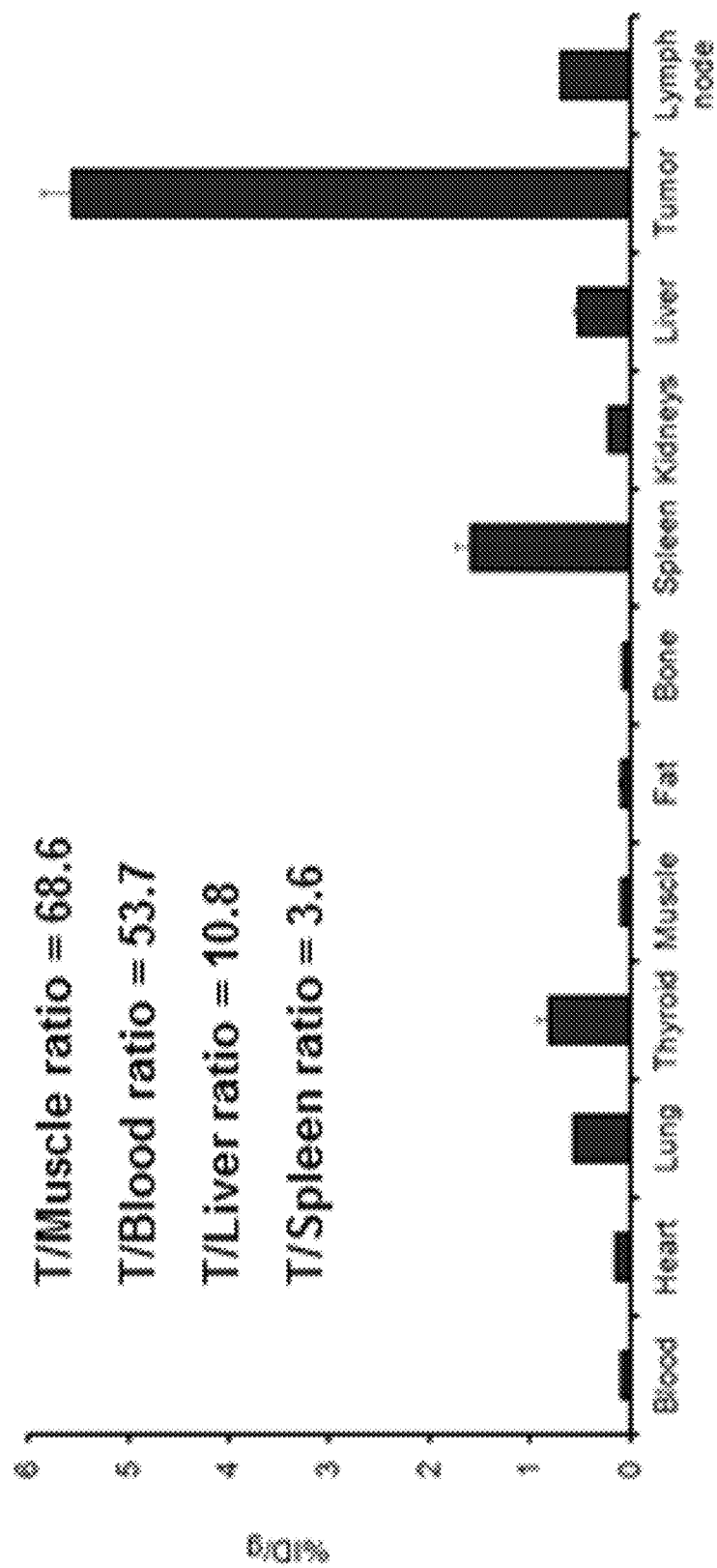
FIG. 7 shows the results evaluating the accumulation amount (% ID/g) of the liposome contrast agent in each tissue 24 hours after administration of the liposome contrast agent according to the present invention to the tail vein of the cervical cancer cell xenograft model.

As can be seen in FIG. 7, the results of the cervical cancer xenograft model using HeLa cells confirmed that the uptake of the tumor, which was 5.5% ID/g, was the highest among other tissues. The ratio of uptake comparing tumor tissues versus other tissues showed even greater differences, indicating it can be utilized to diagnose cervical cancer tissues specifically (tumor-to-muscle ratio=68.6-fold, tumor-to-blood ratio=53.7-fold, tumor-to-liver ratio=10.8, tumor-to-spleen=3.6 fold).

Figure 8:
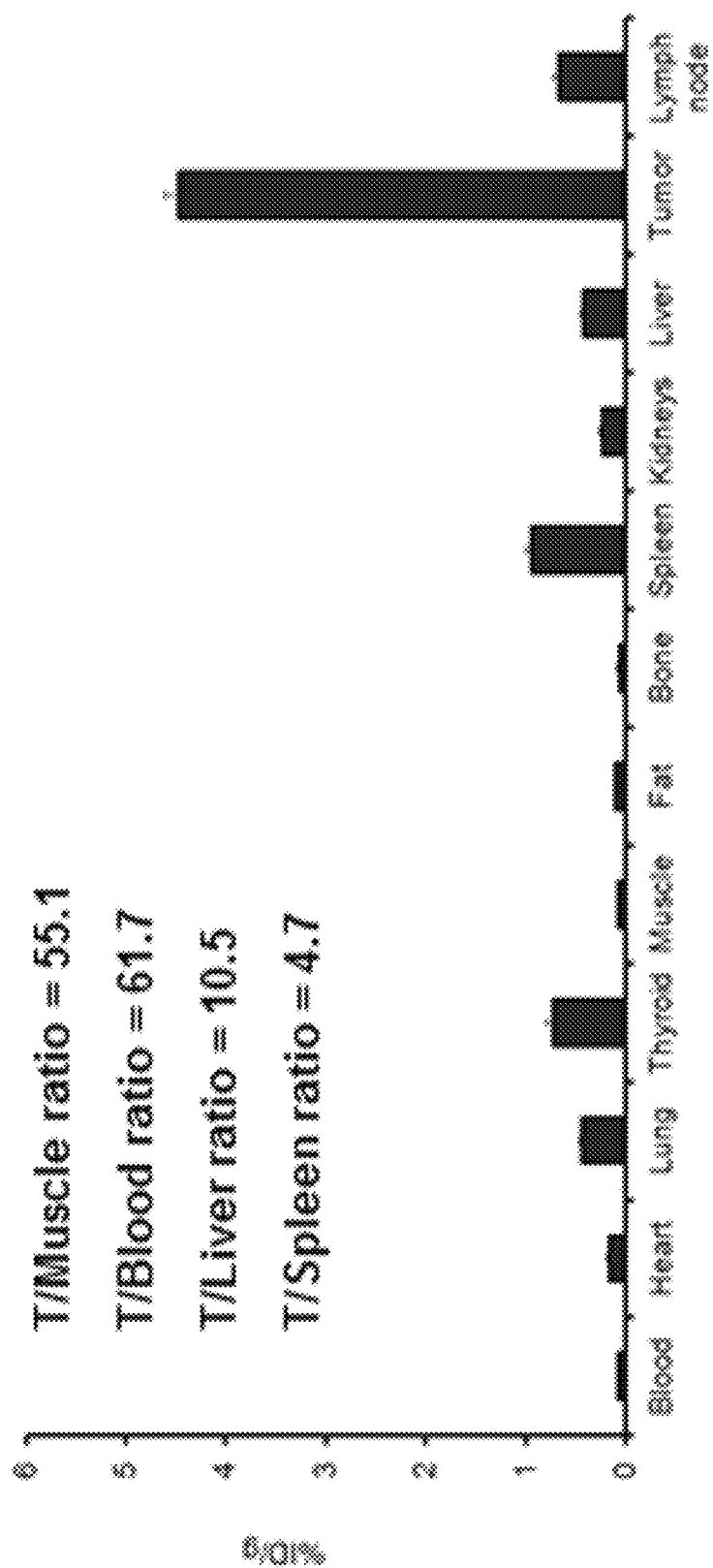
FIG. 8 shows the results evaluating the accumulation amount (% ID/g) of the liposome contrast agent in each tissue 24 hours after administration of the liposome contrast agent according to the present invention to the tail vein of the ovarian cancer cell xenograft model.

As can be seen in FIG. 8, the result for the ovarian cancer xenograft model using SKOV3 cells confirmed that the uptake of the tumor was 4.5% ID/g, highest among the tissues. The ratio of uptake comparing tumor tissues versus other tissues showed even greater differences, indicating it can be utilized to diagnose ovarian cancer tissues specifically (tumor-to-muscle ratio=55.1-fold, tumor-to-blood ratio=61.7-fold, tumor-to-liver ratio=10.5, tumor-to-spleen=4.7 fold).

Figure 9:
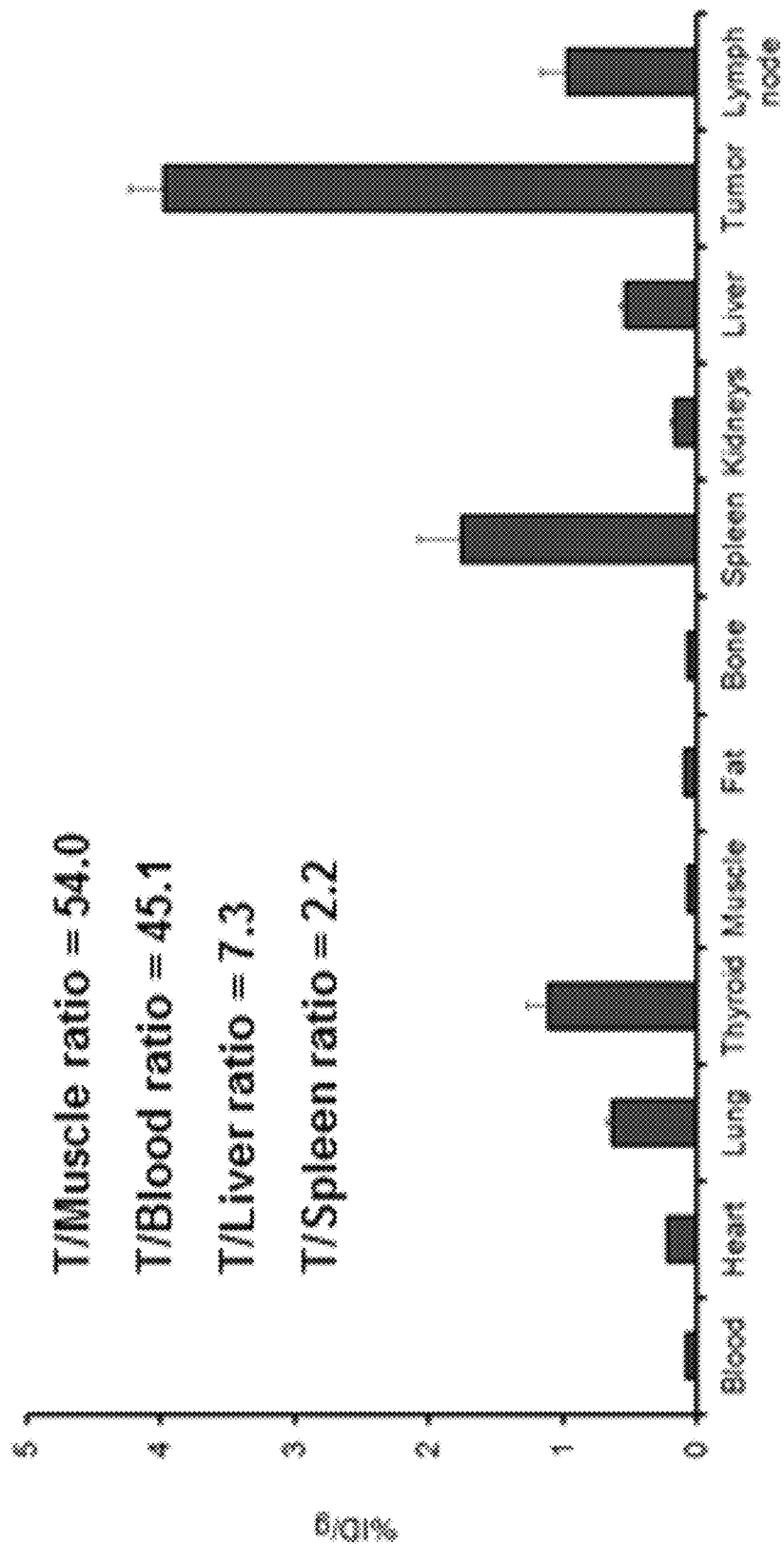
FIG. 9 shows the results evaluating the accumulation amount (% ID/g) of the liposome contrast agent in each tissue 24 hours after administration of the liposome contrast agent according to the present invention to the tail vein of the skin cancer (melanoma) cell xenograft model.

As can be seen in FIG. 9, the result for the ovarian cancer xenograft model using SKOV3 cells showed that the uptake of the tumor was 4.5% ID/g, which was highest among other tissues. Furthermore, the ratio of uptake comparing tumor tissues versus other tissues also showed even larger differences, confirming that it could be used to specifically diagnose ovarian cancer only (tumor-to-muscle ratio=54.0 times, tumor-to-blood ratio=45.1 times, tumor-to-liver ratio=7.3 times, tumor to spleen ratio=2.2).

Figure 10:
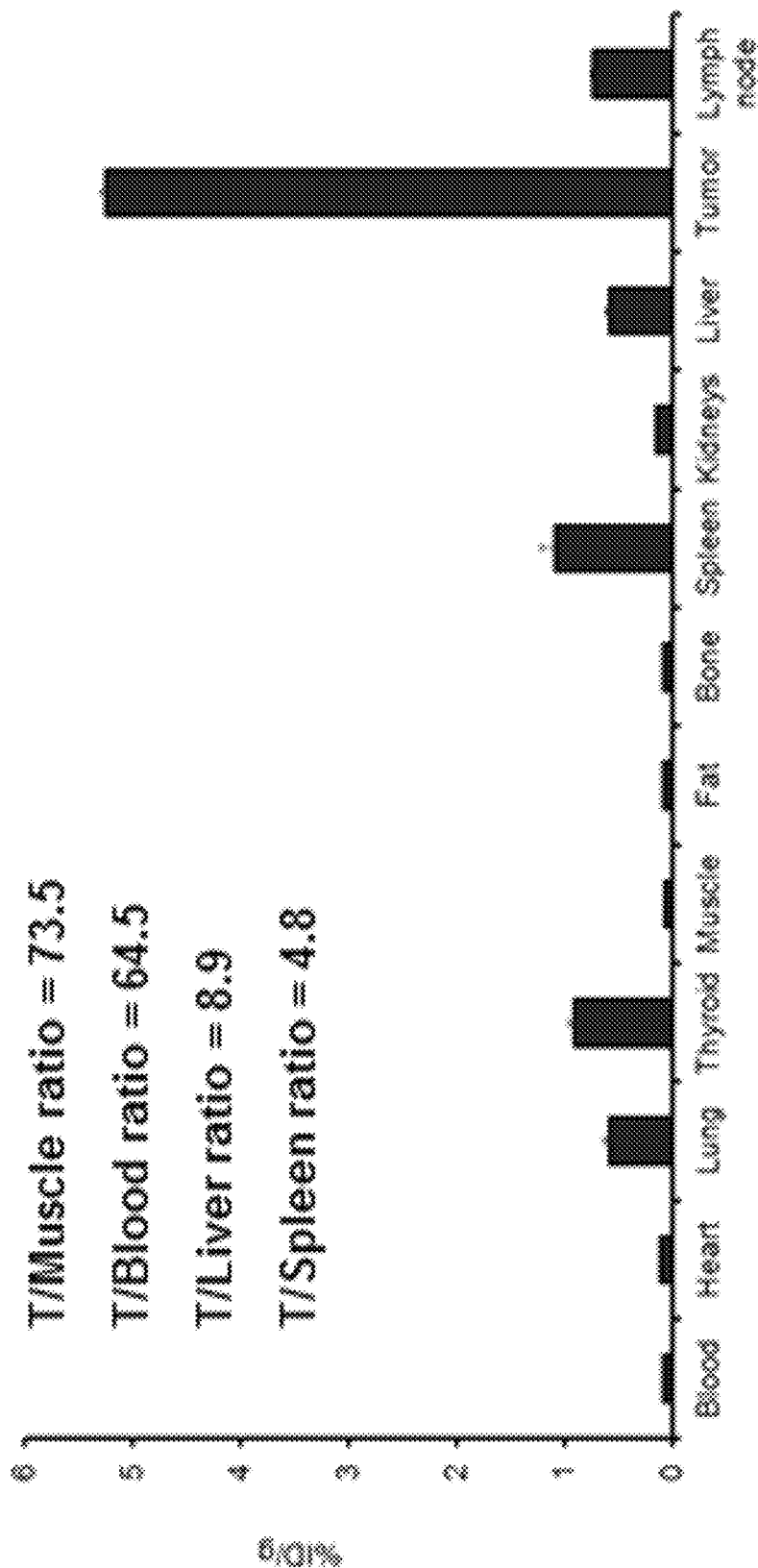
FIG. 10 shows the results evaluating the accumulation amount (% ID/g) of the liposome contrast agent in each tissues 24 hours after administration of the liposome contrast agent according to the present invention to the tail vein of the colon cancer cell xenograft model.

As can be seen in FIG. 10, colorectal cancer xenograft model using CT26 cells generated similar results in that the tumor uptake was 5.2% ID/g, highest among other tissues. In addition, the ratio of uptake comparing tumor tissues versus other tissues also showed even larger differences, confirming that it could be used to specifically diagnose colorectal cancer only (tumor-to-muscle ratio=73.5 times, tumor-to-blood ratio=64.5 times, tumor-to-liver ratio=8.9 times, tumor to spleen ratio=4.8).

On the other hand, the present inventors conducted nuclear imaging experiments using PET besides biodistribution experiments to evaluate whether the liposome contrast agent according to the present invention can be used as a radioactive probe for tumor diagnosis.

Briefly, the liposome contrast agent (folate-[$^{124}$I]HIB-liposome) was injected into the tail vein (200 µCi) of xenograft models of breast cancer cells 4T1, MDA-MB-231 or colorectal cancer cells CT26. PET images were obtained 24 hours after the injection, and results observed.

The results are shown in FIG. 11.

As shown in FIG. 11, it was confirmed that absorption in tissues where reticulum endothelial system (RES) is distributed, such as liver and spleen, was very low and tumor-specific absorption was highest in the PET images. Based on this results, it was again proven that the liposome contrast agent according to the present invention can be very useful for diagnosing tumors overexpressing folate receptors.

5-2: Orthotopic Mouse Model

Figure 12A:
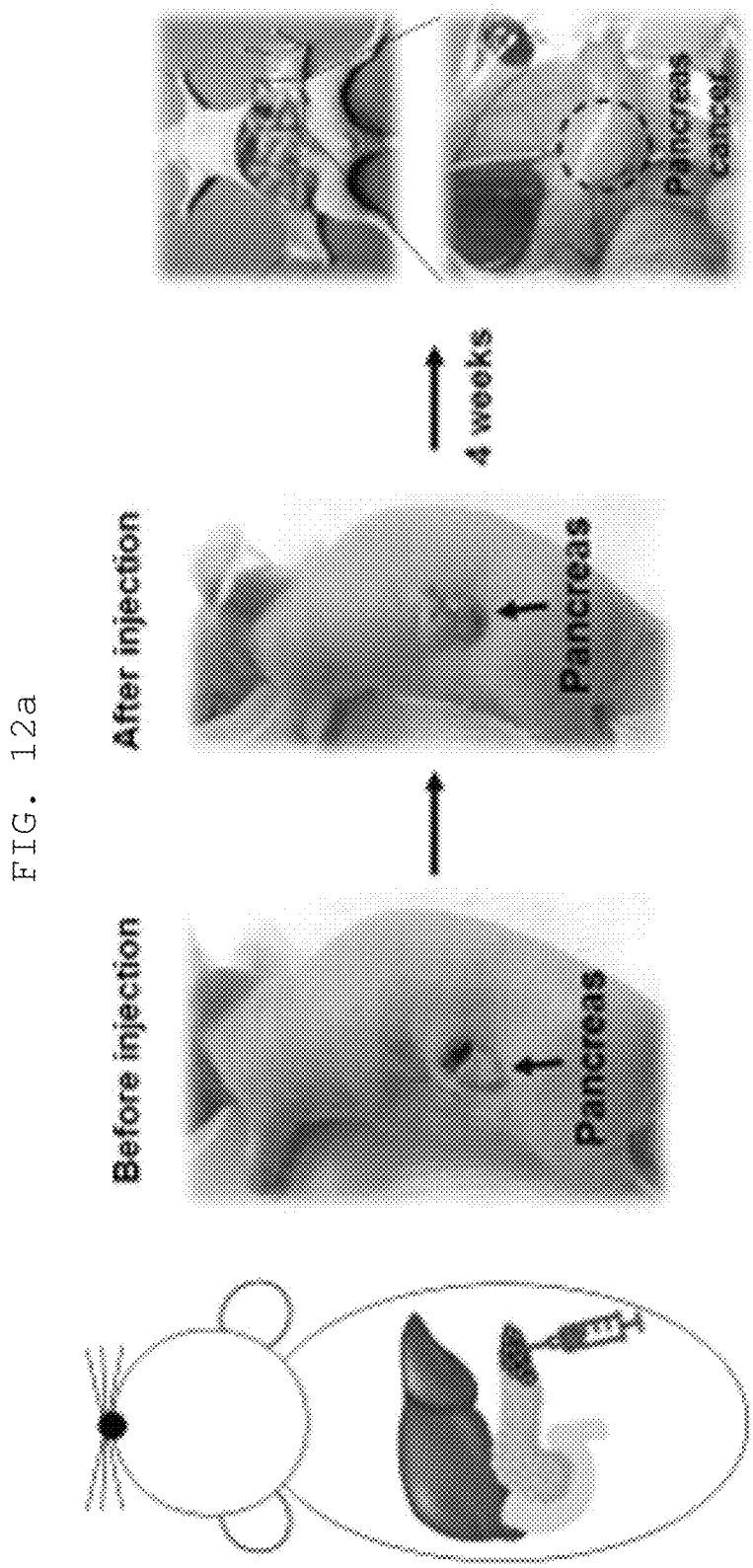
FIG. 12A and FIG. 12B show the establishment process of the pancreatic cancer orthotopic animal model (FIG. 12A), and the images (FIG. 12B) captured using PET and the optical imaging device (IVIS) 24 hours after administration of the liposome contrast agent according to the present invention to the tail vein of the established pancreatic cancer orthotopic animal model.

To evaluate the active target-oriented activity of the liposome contrast agent in the orthotopic model rather than the xenograft model, an orthotopic model of pancreatic cancer was established, and following experiments were conducted (FIG. 12A).

First, we used PANC-1/Luc+ cells expressing luminescence enzymes called luciferase to check the incidence of tumors in the abdominal cavity. These cells were injected at the tip of the pancreas, and 21 days later, it was confirmed that the orthotopic model was well established by luminescence images using IVIS and ensuing experiments were carried out.

PET images were obtained 24 hours after the injection of the liposome contrast agent (folate-[$^{124}$I]HIB-liposome) into the tail vein (200 µCi) of the established pancreatic cancer orthotopic model. Then, when the abdomen was opened, IVIS was used to obtain Cerenkov luminescent images of the liposome contrast agent and a luminescence images using luciferin to identify tumor cells.

Figure 12B:
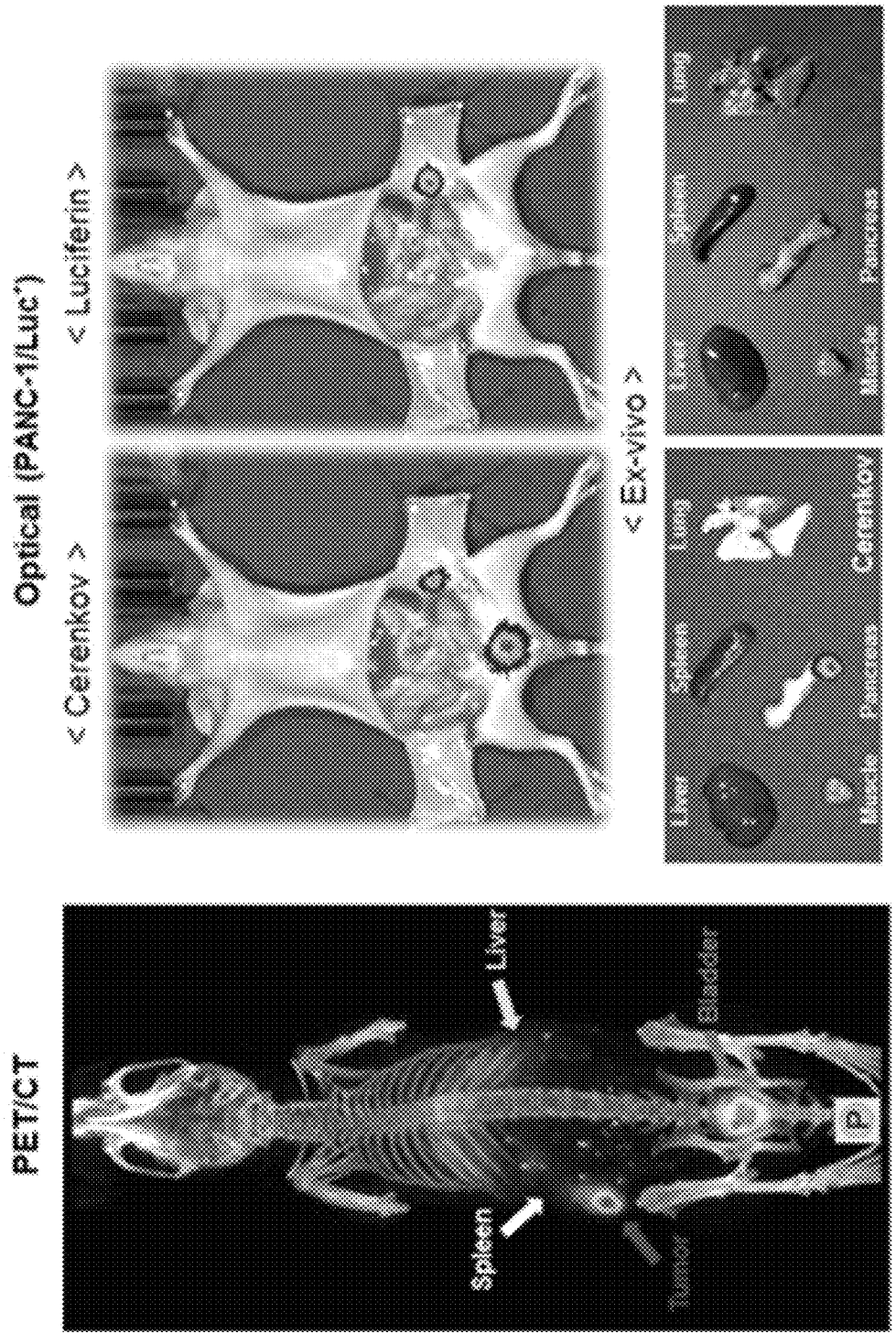

The results are shown in FIG. 12B.

As can be seen in FIG. 12B, it was confirmed that the liposome contrast agent was ingested at a very high concentration in the pancreatic cancer in the PET images. In the luminescence images taken by IVIS when the abdomen was opened, Cerenkov luminescence and luciferin luminescence were detected in the same pancreatic region, directly confirming that the region showing high levels of signal in the PET images was the pancreatic cancer.

Example 6: Evaluation of Tumor Diagnosis Capability in the Breast Cancer Metastasis Model In the case of breast cancer, it is understood that it easily metastasizes to surrounding tissues and other body parts outside the breast, and in particular, metastasis to bone is known to occur frequently.

The present inventors conducted experiments to check whether metastasis of breast cancer can be diagnosed early through PET imaging after 24 hours of injecting the liposome contrast agent according to the present invention.

For the breast cancer metastasis model, MDA-MB-231/Luc+ was used, and after 10 days of direct injection of 1×10$^5$ cells into the left ventricle, IVIS-assisted luminescence images confirmed that bone metastasis occurred to the femoral bones. After verifying the establishment of bone metastasis model of breast cancer, further experiments were carried out (FIG. 12A). PET imaging experiments were performed 24 hours after injection of the liposome contrast agent (folate-[$^{124}$I]HIB-liposome) into the tail vein (200 μCi) of the breast cancer bone metastasis mouse, and PET imaging experiments for comparison using [$^{18}$F]FDG (imaging experiment 1 hour after injection into the tail vein), which is commonly used for tumor diagnosis, were performed in parallel.

The results are shown in FIG. 13B.

As shown in FIG. 13B, in the case of the mice to which the liposome contrast agent according to the present invention was administered, the PET signal was detected in the region exactly matched with the bone metastasis region of the breast cancer cells identified by the luciferin emission image. However, PET images obtained by injecting FDG, which is used as a tumor diagnostic PET probe in the clinic, into the same mouse were difficult to identify the tumor site clearly due to high background uptake.

Meanwhile, a lung metastasis model was prepared by injecting another breast cancer cell 4T1/Luc+ cells (1×10$^5$) into tail vein and establishment of the metastasis model was confirmed by detecting high signals in the lung using luciferin luminescence imaging. After the injection of the liposome contrast agent (folate-[$^{124}$I]HIB-liposome) according to the present invention into the tail vein of the lung metastasis model (200 μCi), the PET was scanned, which showed that lung metastasis can be diagnosed clearly as well. By confirming that the signal is well matched with the signal for metastatic breast cancer cells in the luminescence image, it was determined that the strong signal of the PET images was due to tumor cells metastasized to the lung (FIG. 13C).

INDUSTRIAL APPLICABILITY

As described so far, the present invention relates to a novel liposome-based contrast agent for the inhibition of reticuloendothelial absorption and tumor-specific delivery of radioactive tracers, and more particularly to a liposome contrast agent characterized by consisting of a compound defined by Chemical Formula 1 as a radioactive tracer and lipid, wherein the lipid is characterized by consisting of (a) cholesterol; (b) 1,2-dipalmitoyl-sn-glycero-3-phosphocholine (DPPC); and (c) 1,2-dstearoyl-sn-glycero-3-phosphoethanolamine-N [methoxy (polyethyleneglycol)-2000 (DSPE-PEG2000) and a cancer diagnostic composition containing the same as an active ingredient.

When a liposome system equipped with a contrast agent of Chemical Formula 1 with a unique lipid composition provided by the present invention is prepared, the tumor-to-organ uptake ratio in tumors compared to RES organs is significantly increased, highly enhancing diagnostic efficiency of the compound of Chemical Formula 1 for tumors, therefore it is highly industrially applicable as a diagnostic tool.

What is claimed is:

1. A liposome contrast agent consisting of a compound defined by Chemical Formula 1 and a lipid, wherein the lipid consists of
   (a) cholesterol;
   (b) 1,2-dipalmitoyl-sn-glycero-3-phosphocholine (DPPC); and
   (c) 1,2-distearoyl-sn-glycero-3-phosphoethanolamine-N [methoxy (polyethyleneglycol)-2000] (DSPE-PEG2000):

<Chemical Formula 1>

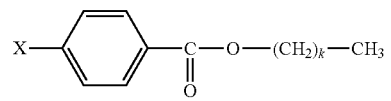

wherein, X is a radioisotope of iodine, and k is in a range of 5≤k≤30, and wherein a molar ratio of (a):(b):(c) is 1:5 to 25:3 to 15.

2. The liposome contrast agent of claim 1, wherein X in the Chemical Formula 1 is a radioisotope of iodine selected from the group of consisting of $^{123}$I, $^{124}$I, $^{125}$I, and $^{131}$I.

3. The liposome contrast agent of claim 1, wherein the compound defined by the Chemical Formula 1 is hexadecyl-4-[$^{131}$I]iodobenzoate defined by Chemical Formula 2:

<Chemical Formula 2>

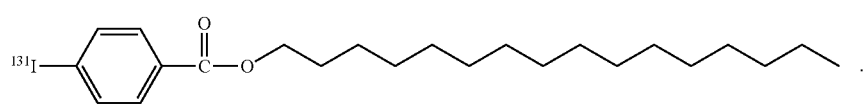

4. A liposome contrast agent consisting of a compound defined by Chemical Formula 1 and a lipid, wherein the lipid consists of:
- (a) cholesterol;
- (b) 1,2-dipalmitoyl-sn-glycero-3-phosphocholine (DPPC); and
- (c-1) 1,2-distearoyl-cn-glycero-3-phosphoethanolamine-N[methoxy(polyethyleneglycol)-2000 (DSPE-PEG2000)]; and
- (c-2) 1,2-distearoyl-sn-glycero-3-phosphoethanolamine-N[methoxy(polyethyleneglycol)-2000-folate] (DSPE-PEG2000-folate):

<Chemical Formula 1>

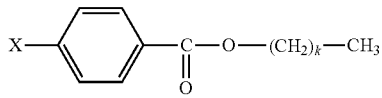

wherein X is a radioisotope of iodine and k is in a range of 5≤k≤30, and wherein a molar ratio of (a):(b):(c-1):(c-2) is 1:5 to 25:2 to 8:1 to 7.

5. The liposome contrast agent of claim 1, wherein the contrast agent is used for optical imaging, positron emission tomography (PET) scanning, or single photon tomography (SPECT) scanning.

6. A method for diagnosing a cancer in a subject suspected for having a cancer, the method comprising:
- imaging the subject by administering an effective amount of a composition comprising the liposome contrast agent of claim 1 to the subject; and
- diagnosing the subject with the cancer based on imaging results.

7. The method of claim 6, wherein absorption of the compound defined by the Chemical Formula 1 is reduced in a reticuloendothelial system and absorption of the compound defined by the Chemical Formula 1 is increased in a folate receptor-overexpressing tumor.

8. The method of claim 7, wherein the folate receptor-overexpressing tumor is selected from the group consisting of pancreatic cancer, breast cancer, ovarian cancer, lung cancer, cervical cancer, colon cancer, melanoma, kidney cancer, brain tumor, myeloid leukemia, and head and neck cancer.

9. The method of claim 8, wherein the folate receptor-overexpressing tumor is pancreatic cancer.

* * * * *